US011213619B2

(12) United States Patent
McLennan et al.

(10) Patent No.: US 11,213,619 B2
(45) Date of Patent: *Jan. 4, 2022

(54) THERMAL MANAGEMENT SYSTEM AND METHOD FOR MEDICAL DEVICES

(71) Applicant: ICU Medical, Inc., San Clemente, CA (US)

(72) Inventors: Kevin P. McLennan, Chicago, IL (US); John C. Hoenninger, III, Deerfield, IL (US)

(73) Assignee: ICU Medical, Inc., San Clemente, CA (US)

( * ) Notice: Subject to any disclaimer, the term of this patent is extended or adjusted under 35 U.S.C. 154(b) by 634 days.

This patent is subject to a terminal disclaimer.

(21) Appl. No.: 16/048,106

(22) Filed: Jul. 27, 2018

(65) Prior Publication Data

US 2019/0192763 A1    Jun. 27, 2019

Related U.S. Application Data (63) Continuation of application No. 15/592,059, filed on May 10, 2017, now Pat. No. 10,034,975, which is a
(Continued)

(51) Int. Cl.
*H05K 7/20* (2006.01)
*A61M 5/14* (2006.01)
(Continued)

(52) U.S. Cl.
CPC ............ *A61M 5/1415* (2013.01); *A61M 5/14* (2013.01); *A61M 5/142* (2013.01); *G06F 1/20* (2013.01);
(Continued)

(58) Field of Classification Search
CPC ...... A61M 5/1415; A61M 5/14; A61M 5/142; A61M 2205/3372; A61M 2209/082; G06F 1/20; H05K 7/20; H05K 7/20436
(Continued)

(56) References Cited

U.S. PATENT DOCUMENTS

| 790,353 A | 5/1905 | Estlingen |
| 1,248,058 A | 11/1917 | Bailey |

(Continued)

FOREIGN PATENT DOCUMENTS

| CA | 2 808 379 | 2/2012 |
| CN | 304975990 | 1/2019 |

(Continued)

OTHER PUBLICATIONS

"CritiCore® Monitor: Critical Fluid Output and Core Bladder Temperature Monitor", BARD Urological Catheter Systems, Advertisement, 2005, pp. 2.

(Continued)

*Primary Examiner* — Anatoly Vortman
*Assistant Examiner* — Zhengfu J Feng
(74) *Attorney, Agent, or Firm* — Knobbe, Martens, Olson & Bear, LLP (57) ABSTRACT

A medical device includes a housing, a power supply, a thermally conductive mounting clamp, a heat shield, and at least one fastener. The housing includes a handle. The power supply is disposed within the housing. The thermally conductive mounting clamp is attached to an outer surface of the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by
(Continued)

the power supply is configured to dissipate from the power supply, through the heat shield, through the at least one fastener, and into the thermally conductive mounting clamp.

18 Claims, 6 Drawing Sheets

Related U.S. Application Data continuation of application No. 14/538,339, filed on Nov. 11, 2014, now abandoned.

(60) Provisional application No. 61/902,495, filed on Nov. 11, 2013.

(51) Int. Cl.
*A61M 5/142* (2006.01)
*G06F 1/20* (2006.01)

(52) U.S. Cl.
CPC ........... *H05K 7/20* (2013.01); *H05K 7/20436* (2013.01); *A61M 2205/3372* (2013.01); *A61M 2209/082* (2013.01)

(58) Field of Classification Search
USPC ........................................................ 361/707
See application file for complete search history.

(56) References Cited

U.S. PATENT DOCUMENTS

| | | |
|---|---|---|
| 1,576,445 A | 3/1926 | Mitchell |
| 1,647,039 A | 4/1927 | Fischer |
| 1,749,491 A | 4/1930 | Kokay |
| 2,820,886 A | 5/1955 | Posey |
| 2,869,690 A | 1/1959 | Winters et al. |
| 2,903,165 A | 9/1959 | Hanson et al. |
| 3,185,153 A | 5/1965 | Leucci |
| 3,316,935 A | 5/1967 | Kaiser et al. |
| 3,367,270 A | 2/1968 | Schlosser |
| 3,427,986 A | 2/1969 | Corneil |
| 3,606,596 A | 9/1971 | Edwards |
| 3,647,176 A | 3/1972 | Usry |
| 3,650,296 A | 3/1972 | Johnson et al. |
| 3,771,862 A | 11/1973 | Land et al. |
| 3,777,581 A | 12/1973 | Sartori |
| 3,812,482 A | 5/1974 | Clark |
| 3,898,637 A | 8/1975 | Wolstenholme |
| 3,901,231 A * | 8/1975 | Olson .............. A61M 5/14216 604/152 |
| 3,913,384 A | 10/1975 | Furuya |
| 3,921,622 A | 11/1975 | Cole |
| 3,935,876 A | 2/1976 | Massie et al. |
| 3,985,133 A * | 10/1976 | Jenkins ................ A61M 5/172 604/67 |
| 4,068,521 A | 1/1978 | Cosentino et al. |
| 4,155,362 A | 5/1979 | Jess |
| 4,187,057 A | 2/1980 | Xanthopoulos |
| 4,193,635 A | 3/1980 | Thiruvengadam et al. |
| 4,195,515 A | 4/1980 | Smoll |
| 4,211,380 A | 7/1980 | Lillegard et al. |
| 4,213,454 A | 7/1980 | Shim |
| 4,223,813 A | 9/1980 | Garrett et al. |
| 4,236,880 A | 12/1980 | Archibald |
| 4,240,294 A | 12/1980 | Grande |
| 4,244,365 A | 1/1981 | McGill |
| 4,261,356 A | 4/1981 | Turner et al. |
| 4,291,701 A | 9/1981 | Bowman et al. |
| 4,303,376 A | 12/1981 | Siekmann |
| 4,332,378 A | 6/1982 | Pryor |
| 4,343,316 A | 8/1982 | Jespersen |
| 4,381,591 A | 5/1983 | Barger et al. |
| 4,397,642 A | 8/1983 | Lamadrid |
| 4,397,648 A | 8/1983 | Knute et al. |
| 4,406,042 A | 9/1983 | McPhee et al. |
| 4,418,565 A | 12/1983 | St. John |
| 4,439,179 A | 3/1984 | Lueders et al. |
| 4,468,222 A | 8/1984 | Lundquist |
| 4,469,765 A | 9/1984 | McCartney et al. |
| 4,482,347 A | 11/1984 | Borsanyi |
| 4,496,351 A | 1/1985 | Hillel et al. |
| 4,513,885 A | 4/1985 | Hogan |
| 4,528,847 A | 7/1985 | Halmi |
| 4,530,647 A | 7/1985 | Uno |
| 4,551,134 A | 11/1985 | Slavik et al. |
| 4,565,500 A | 1/1986 | Jeensalute et al. |
| 4,573,968 A | 3/1986 | Parker |
| 4,585,441 A | 4/1986 | Archibald et al. |
| 4,586,691 A | 5/1986 | Kozlow |
| 4,589,171 A | 5/1986 | McGill et al. |
| 4,607,520 A | 8/1986 | Dam |
| 4,613,325 A | 9/1986 | Abrams |
| 4,626,243 A | 12/1986 | Singh et al. |
| 4,626,244 A | 12/1986 | Reinicke |
| 4,644,960 A | 2/1987 | Johans |
| 4,680,977 A | 7/1987 | Conero et al. |
| 4,681,563 A | 7/1987 | Deckert et al. |
| 4,683,916 A | 8/1987 | Raines |
| 4,689,043 A | 8/1987 | Bisha |
| 4,694,273 A | 9/1987 | Franchino |
| 4,696,671 A | 9/1987 | Epstein et al. |
| 4,722,725 A | 2/1988 | Sawyer |
| 4,728,265 A | 3/1988 | Cannon |
| 4,735,558 A | 4/1988 | Kienholz et al. |
| 4,756,706 A | 7/1988 | Kerns et al. |
| 4,758,228 A | 7/1988 | Williams |
| 4,802,650 A | 2/1989 | Stricker |
| 4,811,928 A | 3/1989 | Iwatschenko et al. |
| 4,813,280 A | 3/1989 | Miller et al. |
| 4,820,281 A | 4/1989 | Lawler |
| 4,828,545 A | 5/1989 | Epstein et al. |
| 4,832,299 A | 5/1989 | Gorton et al. |
| 4,840,345 A | 6/1989 | Neil et al. |
| 4,842,584 A | 6/1989 | Pastrone et al. |
| 4,844,397 A | 7/1989 | Skakoon et al. |
| 4,845,487 A | 7/1989 | Frantz et al. |
| 4,846,636 A | 7/1989 | Danby et al. |
| 4,856,339 A | 8/1989 | Williams |
| 4,857,048 A | 8/1989 | Simons et al. |
| 4,857,050 A | 8/1989 | Lentz et al. |
| 4,858,548 A | 8/1989 | Echeverria |
| 4,865,584 A | 9/1989 | Epstein et al. |
| 4,881,413 A | 11/1989 | Georgi et al. |
| D305,060 S | 12/1989 | Bisha' et al. |
| 4,892,656 A | 1/1990 | Pietzsch |
| 4,898,578 A | 2/1990 | Rubalcaba, Jr. |
| 4,925,444 A | 5/1990 | Orkin et al. |
| 4,927,411 A | 5/1990 | Pastrone et al. |
| 4,935,014 A | 6/1990 | Haber |
| 4,938,079 A | 7/1990 | Goldberg |
| 4,947,856 A | 8/1990 | Beard |
| 5,014,798 A | 5/1991 | Glynn |
| 5,017,192 A | 5/1991 | Dodge et al. |
| 5,031,465 A | 7/1991 | Redus |
| 5,034,004 A | 7/1991 | Crankshaw |
| 5,062,775 A | 11/1991 | Orth |
| 5,085,644 A | 2/1992 | Watson et al. |
| 5,098,262 A | 3/1992 | Wecker et al. |
| 5,102,083 A | 4/1992 | Baskas |
| 5,102,392 A | 4/1992 | Sakai et al. |
| 5,113,904 A | 5/1992 | Aslanian |
| 5,138,743 A | 8/1992 | Hoffman |
| 5,125,891 A | 9/1992 | Hossain et al. |
| 5,152,753 A | 10/1992 | Laguette et al. |
| 5,154,513 A | 10/1992 | Beer |
| 5,163,900 A | 11/1992 | Wortrich |
| 5,165,406 A | 11/1992 | Wong et al. |
| 5,165,873 A | 11/1992 | Meijer |
| 5,169,106 A | 12/1992 | Rasmussen |
| 5,177,993 A | 1/1993 | Beckman et al. |
| 5,187,746 A | 2/1993 | Narisawa |
| 5,192,269 A | 3/1993 | Poli et al. |
| 5,205,153 A | 4/1993 | Hlavinka et al. |

(56) References Cited

U.S. PATENT DOCUMENTS

| | | |
|---|---|---|
| 5,207,642 A | 5/1993 | Orkin et al. |
| 5,211,626 A | 5/1993 | Frank et al. |
| 5,217,355 A | 6/1993 | Hyman et al. |
| 5,219,099 A | 6/1993 | Spence et al. |
| 5,219,327 A | 6/1993 | Okada |
| 5,219,428 A | 6/1993 | Stern |
| 5,220,920 A | 6/1993 | Gharib |
| 5,225,063 A | 7/1993 | Gumbrecht et al. |
| 5,242,406 A | 9/1993 | Gross et al. |
| 5,256,157 A | 10/1993 | Samiotes et al. |
| 5,257,978 A | 11/1993 | Haber et al. |
| 5,270,702 A | 12/1993 | Krolak |
| 5,271,815 A | 12/1993 | Wong |
| 5,282,787 A | 2/1994 | Wortrich |
| 5,287,851 A | 2/1994 | Beran et al. |
| 5,292,306 A | 3/1994 | Wynkoop et al. |
| 5,302,093 A | 4/1994 | Owens et al. |
| 5,306,122 A | 4/1994 | Gebauer et al. |
| 5,309,604 A | 5/1994 | Poulsen et al. |
| 5,317,506 A | 5/1994 | Coutre et al. |
| D348,101 S | 6/1994 | Poli et al. |
| 5,322,253 A | 6/1994 | Stevens |
| 5,324,266 A | 6/1994 | Ambrisco et al. |
| 5,325,728 A | 7/1994 | Zimmerman et al. |
| 5,326,059 A | 7/1994 | Pryor et al. |
| 5,330,634 A | 7/1994 | Wong et al. |
| 5,332,184 A | 7/1994 | Davis |
| 5,345,932 A | 9/1994 | Yafuso et al. |
| 5,346,466 A | 9/1994 | Yerlikaya et al. |
| 5,358,205 A | 10/1994 | Starkey et al. |
| 5,364,364 A | 11/1994 | Kasvikis et al. |
| D353,667 S | 12/1994 | Tsubota et al. |
| 5,378,126 A | 1/1995 | Abrahamson et al. |
| 5,378,231 A | 1/1995 | Johnson et al. |
| 5,380,665 A | 1/1995 | Cusack et al. |
| 5,382,232 A | 1/1995 | Hague et al. |
| D355,716 S | 2/1995 | Nash et al. |
| 5,395,320 A * | 3/1995 | Padda ............... A61M 5/14228 128/DIG. 12 |
| 5,401,256 A | 3/1995 | Stone et al. |
| 5,403,277 A | 4/1995 | Dodge et al. |
| 5,417,119 A | 5/1995 | Smoll |
| 5,417,395 A | 5/1995 | Fowler et al. |
| 5,421,209 A | 6/1995 | Redus |
| 5,421,328 A | 6/1995 | Bedingham |
| 5,431,174 A | 7/1995 | Knute |
| 5,431,509 A | 7/1995 | Anderson et al. |
| 5,431,627 A | 7/1995 | Pastrone et al. |
| 5,437,635 A | 8/1995 | Fields et al. |
| 5,445,506 A | 8/1995 | Afflerbaugh et al. |
| 5,445,621 A | 8/1995 | Poli et al. |
| 5,445,622 A | 8/1995 | Brown |
| 5,450,758 A | 9/1995 | Smoll |
| 5,453,098 A | 9/1995 | Botts et al. |
| 5,462,052 A | 10/1995 | Gehrich |
| 5,462,256 A | 10/1995 | Minick et al. |
| 5,463,906 A | 11/1995 | Spani et al. |
| 5,465,938 A | 11/1995 | Werge et al. |
| 5,482,446 A | 1/1996 | Williamson et al. |
| D367,528 S | 2/1996 | Martson et al. |
| 5,489,265 A | 2/1996 | Montalvo et al. |
| 5,489,486 A | 2/1996 | Glover |
| 5,505,828 A | 4/1996 | Wong et al. |
| 5,515,713 A | 5/1996 | Saugues et al. |
| 5,524,475 A | 6/1996 | Kolpak |
| 5,527,289 A | 6/1996 | Foster et al. |
| 5,538,807 A | 7/1996 | Hagiuda |
| 5,540,561 A | 7/1996 | Johnson et al. |
| 5,551,300 A | 9/1996 | Vurek et al. |
| 5,554,013 A | 9/1996 | Owens et al. |
| 5,554,112 A | 9/1996 | Walbrink et al. |
| D376,199 S | 12/1996 | Rozek et al. |
| 5,584,671 A | 12/1996 | Schweitzer, Jr. et al. |
| 5,586,868 A | 12/1996 | Lawless et al. |
| 5,601,420 A | 2/1997 | Warner et al. |
| 5,601,445 A | 2/1997 | Schipper et al. |
| 5,603,613 A | 2/1997 | Butterfield et al. |
| 5,609,572 A | 3/1997 | Lang |
| 5,611,784 A | 3/1997 | Barresi et al. |
| 5,616,124 A * | 4/1997 | Hague ............... A61M 5/365 128/DIG. 13 |
| 5,626,151 A | 5/1997 | Linden |
| 5,628,309 A | 5/1997 | Brown |
| 5,628,731 A | 5/1997 | Dodge et al. |
| 5,630,710 A | 5/1997 | Tune et al. |
| 5,647,491 A | 7/1997 | Foster et al. |
| 5,647,852 A | 7/1997 | Atkinson |
| 5,651,775 A | 7/1997 | Walker et al. |
| 5,657,000 A | 8/1997 | Ellingboe |
| 5,658,133 A | 8/1997 | Anderson et al. |
| 5,672,832 A | 9/1997 | Cucci et al. |
| 5,673,588 A | 10/1997 | Raymond |
| 5,681,019 A | 10/1997 | Boyce |
| 5,693,891 A | 12/1997 | Brown et al. |
| 5,697,899 A | 12/1997 | Hillman et al. |
| 5,697,916 A | 12/1997 | Schraga |
| 5,709,663 A | 1/1998 | Younkes |
| D390,574 S | 2/1998 | Ashcraft |
| D390,654 S | 2/1998 | Alsberg et al. |
| 5,713,509 A | 2/1998 | Correll |
| 5,713,856 A | 2/1998 | Eggers et al. |
| 5,718,569 A | 2/1998 | Holst |
| 5,723,773 A | 3/1998 | Bryan |
| 5,728,069 A | 3/1998 | Montevecchi et al. |
| 5,728,074 A | 3/1998 | Castellano et al. |
| 5,733,061 A | 3/1998 | Child |
| 5,736,650 A | 4/1998 | Hiron et al. |
| 5,738,662 A | 4/1998 | Shannon et al. |
| 5,740,810 A | 4/1998 | Johnson et al. |
| 5,745,378 A | 4/1998 | Barker et al. |
| D394,440 S | 5/1998 | Chen |
| 5,752,918 A | 5/1998 | Fowler et al. |
| 5,755,563 A | 5/1998 | Clegg et al. |
| 5,755,683 A | 5/1998 | Houle et al. |
| 5,758,643 A | 6/1998 | Wong et al. |
| 5,763,760 A | 6/1998 | Gumbrecht et al. |
| 5,772,166 A | 6/1998 | Adams |
| 5,772,637 A | 6/1998 | Heinzmann et al. |
| 5,782,611 A | 7/1998 | Neftel et al. |
| 5,782,805 A * | 7/1998 | Meinzer ............... A61M 5/172 604/131 |
| 5,793,216 A | 8/1998 | Constant |
| 5,804,048 A | 9/1998 | Wong et al. |
| 5,805,455 A | 9/1998 | Lipps |
| 5,807,345 A | 9/1998 | Grabenkort |
| 5,812,419 A | 9/1998 | Chupp et al. |
| 5,814,015 A | 9/1998 | Gargano et al. |
| 5,816,779 A | 10/1998 | Lawless et al. |
| 5,848,971 A | 12/1998 | Fowler et al. |
| 5,853,386 A | 12/1998 | Davis et al. |
| 5,868,696 A | 2/1999 | Giesler et al. |
| 5,868,710 A | 2/1999 | Battiato et al. |
| 5,868,712 A | 2/1999 | Briggs et al. |
| 5,891,051 A | 4/1999 | Han et al. |
| 5,895,371 A | 4/1999 | Levitas et al. |
| 5,902,253 A | 5/1999 | Pfeiffer et al. |
| 5,904,666 A | 5/1999 | DeDecker et al. |
| 5,910,808 A | 6/1999 | Fukasawa et al. |
| 5,925,022 A | 7/1999 | Battiato et al. |
| 5,932,175 A | 8/1999 | Knute et al. |
| 5,935,099 A | 8/1999 | Peterson et al. |
| 5,938,638 A | 8/1999 | Passariello et al. |
| 5,939,326 A | 8/1999 | Chupp et al. |
| 5,941,846 A | 8/1999 | Duffy et al. |
| 5,944,660 A | 8/1999 | Kimball et al. |
| 5,947,911 A | 9/1999 | Wong et al. |
| 5,954,485 A | 9/1999 | Johnson et al. |
| 5,989,222 A | 11/1999 | Cole et al. |
| 6,004,292 A | 12/1999 | Battiato et al. |
| 6,007,941 A | 12/1999 | Hermann et al. |
| 6,017,318 A | 1/2000 | Gauthier et al. |
| 6,027,445 A | 2/2000 | Von Bahr |
| 6,027,479 A | 2/2000 | Alei et al. |
| 6,032,536 A | 3/2000 | Peeters et al. |

(56) References Cited

U.S. PATENT DOCUMENTS

| | | |
|---|---|---|
| D424,692 S | 5/2000 | Monaghan et al. |
| 6,056,522 A | 5/2000 | Johnson |
| 6,068,615 A | 5/2000 | Brown et al. |
| 6,080,583 A | 6/2000 | Von Bahr |
| 6,085,574 A | 7/2000 | Neftel et al. |
| 6,090,071 A | 7/2000 | Kriesel et al. |
| 6,099,470 A | 8/2000 | Bahr |
| 6,105,442 A | 8/2000 | Kriesel et al. |
| 6,106,498 A | 8/2000 | Friedli et al. |
| 6,109,460 A | 8/2000 | Herlevi et al. |
| 6,110,153 A | 8/2000 | Davis |
| 6,110,410 A | 8/2000 | Owens et al. |
| RE36,871 E | 9/2000 | Epstein et al. |
| 6,117,290 A | 9/2000 | Say et al. |
| 6,123,827 A | 9/2000 | Wong et al. |
| 6,165,154 A | 12/2000 | Gray et al. |
| 6,186,752 B1 | 2/2001 | Deniega et al. |
| 6,186,977 B1 | 2/2001 | Andrews et al. |
| 6,186,983 B1 | 2/2001 | Von Bahr |
| 6,203,528 B1 | 3/2001 | Deckert |
| 6,210,361 B1 | 4/2001 | Kamen et al. |
| 6,221,065 B1 | 4/2001 | Davis |
| 6,231,320 B1 | 5/2001 | Lawless et al. |
| 6,237,398 B1 | 5/2001 | Porat et al. |
| 6,250,132 B1 | 6/2001 | Drzewiecki |
| 6,254,572 B1 | 7/2001 | Knipfer et al. |
| 6,261,262 B1 | 7/2001 | Briggs |
| 6,269,704 B1 | 8/2001 | Ziv et al. |
| 6,270,455 B1 | 8/2001 | Brown |
| 6,272,934 B1 | 8/2001 | Rajan et al. |
| 6,277,099 B1 | 8/2001 | Strowe et al. |
| 6,285,155 B1 | 9/2001 | Maske et al. |
| 6,290,681 B1 | 9/2001 | Brown |
| 6,325,264 B1 | 12/2001 | Omosako |
| 6,349,740 B1 | 2/2002 | Cho et al. |
| D454,884 S | 3/2002 | Christiansen et al. |
| 6,364,857 B1 | 4/2002 | Gray et al. |
| 6,385,505 B1 | 5/2002 | Lipps |
| 6,386,050 B1 | 5/2002 | Yin et al. |
| 6,390,120 B1 | 5/2002 | Guala |
| 6,396,583 B1 | 5/2002 | Clare |
| 6,409,707 B1 | 6/2002 | Guala |
| 6,422,256 B1 | 7/2002 | Balazy et al. |
| 6,445,053 B1 | 9/2002 | Cho |
| 6,463,394 B1 | 10/2002 | Von Bahr |
| 6,464,667 B1 | 10/2002 | Kamen et al. |
| 6,478,065 B1 | 11/2002 | Haberstroh et al. |
| 6,482,185 B1 | 11/2002 | Hartmann |
| 6,488,652 B1 | 12/2002 | Weijand et al. |
| 6,489,896 B1 | 12/2002 | Platt |
| 6,494,694 B2 | 12/2002 | Lawless et al. |
| 6,503,221 B1 | 1/2003 | Briggs |
| 6,515,487 B1 | 2/2003 | Dawson |
| 6,519,569 B1 | 2/2003 | White et al. |
| 6,537,258 B1 | 3/2003 | Guala |
| 6,558,125 B1 | 5/2003 | Futterknecht |
| 6,565,054 B2 | 5/2003 | Weesner et al. |
| 6,568,416 B2 | 5/2003 | Tucker et al. |
| D475,721 S | 6/2003 | Harper et al. |
| 6,578,435 B2 | 6/2003 | Gould et al. |
| RE38,189 E | 7/2003 | Walker et al. |
| 6,595,943 B1 | 7/2003 | Burbank |
| 6,599,746 B1 | 7/2003 | Gumbrecht |
| 6,609,047 B1 | 8/2003 | Lipps |
| D479,248 S | 9/2003 | Gist et al. |
| 6,623,470 B2 | 9/2003 | Munis et al. |
| D481,121 S | 10/2003 | Evans |
| 6,635,033 B1 | 10/2003 | Hill et al. |
| 6,645,142 B2 | 11/2003 | Braig et al. |
| 6,656,148 B2 | 12/2003 | Das et al. |
| D485,356 S | 1/2004 | Evans |
| 6,672,561 B2 | 1/2004 | Kerg et al. |
| 6,685,668 B1 | 2/2004 | Cho et al. |
| 6,685,670 B2 | 2/2004 | Miles et al. |
| 6,685,678 B2 | 2/2004 | Evans et al. |
| 6,695,803 B1 | 2/2004 | Robinson et al. |
| 6,700,174 B1 | 3/2004 | Mui et al. |
| 6,700,784 B2 | 3/2004 | Huang et al. |
| 6,709,417 B1 | 3/2004 | Houle et al. |
| 6,722,211 B1 | 4/2004 | Ciobanu et al. |
| 6,726,656 B2 | 4/2004 | Kamen et al. |
| 6,726,657 B2 | 4/2004 | Dedig et al. |
| 6,736,801 B1 | 5/2004 | Gallagher |
| 6,749,403 B2 | 6/2004 | Bryant et al. |
| 6,755,086 B2 | 6/2004 | Salamitou |
| 6,755,391 B2 | 6/2004 | Newton et al. |
| 6,760,643 B2 | 7/2004 | Lipps |
| 6,813,964 B1 | 11/2004 | Clark et al. |
| D500,326 S | 12/2004 | Fathallah et al. |
| 6,827,709 B2 | 12/2004 | Fujii |
| 6,872,297 B2 | 3/2005 | Mansouri et al. |
| D504,507 S | 4/2005 | Ziegler et al. |
| 6,890,315 B1 | 5/2005 | Levin et al. |
| 6,905,314 B2 | 6/2005 | Danby |
| 6,915,679 B2 | 7/2005 | Chien et al. |
| 6,920,795 B2 | 7/2005 | Bischoff et al. |
| 6,929,619 B2 | 8/2005 | Fago et al. |
| 6,932,796 B2 | 8/2005 | Sage et al. |
| 6,935,189 B2 | 8/2005 | Richards |
| 6,935,192 B2 | 8/2005 | Sobek et al. |
| 6,939,111 B2 | 9/2005 | Huitt et al. |
| 6,942,473 B2 | 9/2005 | Abrahamson et al. |
| 6,942,636 B2 | 9/2005 | Holst et al. |
| 6,964,204 B2 | 11/2005 | Clark et al. |
| 6,969,419 B1 | 11/2005 | Macemon |
| 6,975,922 B2 | 12/2005 | Duncan et al. |
| 6,981,960 B2 | 1/2006 | Cho et al. |
| D515,205 S | 2/2006 | Fathalla et al. |
| 7,004,727 B2 | 2/2006 | Kline et al. |
| 7,008,393 B2 | 3/2006 | Robinson et al. |
| RE39,075 E | 4/2006 | Verkaart |
| 7,029,105 B2 | 4/2006 | Matsuba et al. |
| 7,037,428 B1 | 5/2006 | Robinson et al. |
| 7,041,076 B1 | 5/2006 | Westberg et al. |
| 7,044,002 B2 | 5/2006 | Ericson et al. |
| 7,059,184 B2 | 6/2006 | Kanouda et al. |
| 7,061,766 B2 | 6/2006 | Wainwright et al. |
| 7,070,578 B2 | 7/2006 | Leukanech et al. |
| 7,074,209 B2 | 7/2006 | Evans et al. |
| 7,077,650 B2 | 7/2006 | Johnstone |
| 7,082,843 B2 | 8/2006 | Clark et al. |
| 7,087,036 B2 | 8/2006 | Busby et al. |
| 7,096,729 B2 | 8/2006 | Repko et al. |
| 7,115,113 B2 | 10/2006 | Evans et al. |
| 7,140,070 B2 | 11/2006 | Yuta et al. |
| 7,152,469 B2 | 12/2006 | Milleker et al. |
| 7,160,087 B2 | 1/2007 | Fathallah et al. |
| 7,161,488 B2 | 1/2007 | Frasch |
| 7,162,290 B1 | 1/2007 | Levin |
| 7,162,927 B1 | 1/2007 | Selvan et al. |
| 7,169,128 B2 | 1/2007 | Kriesel et al. |
| 7,190,275 B2 | 3/2007 | Goldberg et al. |
| 7,258,534 B2 | 8/2007 | Fathallah et al. |
| 7,327,273 B2 | 2/2008 | Hung et al. |
| 7,364,562 B2 | 4/2008 | Braig et al. |
| 7,367,942 B2 | 5/2008 | Grage et al. |
| 7,377,148 B2 | 5/2008 | Cassidy et al. |
| 7,415,895 B2 | 8/2008 | Kurisaki et al. |
| 7,462,161 B2 | 12/2008 | O'Mahony et al. |
| 7,503,903 B2 | 3/2009 | Carlisle et al. |
| 7,556,616 B2 | 7/2009 | Fathallah et al. |
| 7,571,024 B2 | 8/2009 | Duncan et al. |
| 7,608,042 B2 | 10/2009 | Golberger et al. |
| 7,615,007 B2 | 11/2009 | Shults et al. |
| 7,621,892 B2 | 11/2009 | Fago et al. |
| 7,693,697 B2 | 4/2010 | Westenskow et al. |
| 7,707,897 B2 | 5/2010 | Ong |
| 7,722,537 B2 | 5/2010 | Sterling et al. |
| 7,766,630 B2 | 8/2010 | Fathallah et al. |
| 7,771,389 B2 | 8/2010 | Grispo et al. |
| 7,775,126 B2 | 8/2010 | Eckhardt |
| 7,775,127 B2 | 8/2010 | Wade |
| 7,784,330 B2 | 8/2010 | Angelescu et al. |
| 7,810,401 B2 | 10/2010 | Brown et al. |

(56) References Cited

U.S. PATENT DOCUMENTS

| | | |
|---|---|---|
| 7,819,838 B2 | 10/2010 | Ziegler et al. |
| 7,846,131 B2 | 12/2010 | Hudson et al. |
| 7,850,659 B1 | 12/2010 | Trombley, III et al. |
| 7,866,201 B1 | 1/2011 | Tutu et al. |
| 7,884,735 B2 | 2/2011 | Newkirk |
| 7,895,053 B2 | 2/2011 | Holland et al. |
| 7,896,572 B2 | 3/2011 | Fathallah et al. |
| 7,905,710 B2 | 3/2011 | Wang et al. |
| 7,933,780 B2 | 4/2011 | de la Huerga |
| 7,935,077 B2 | 5/2011 | Thor et al. |
| 7,972,296 B2 | 7/2011 | Braig et al. |
| 7,975,491 B2 | 7/2011 | Smission et al. |
| 7,976,508 B2 | 7/2011 | Hoag |
| 7,998,115 B2 | 8/2011 | Bedingfield et al. |
| 8,033,157 B2 | 10/2011 | Yardimci et al. |
| 8,048,022 B2 | 11/2011 | Moy et al. |
| 8,052,644 B2 | 11/2011 | Radgowski et al. |
| 8,057,437 B2 | 11/2011 | Ziegler et al. |
| 8,061,219 B2 | 11/2011 | Rezgui et al. |
| 8,065,161 B2 | 11/2011 | Howard et al. |
| 8,065,924 B2 | 11/2011 | Ziegler et al. |
| 8,105,269 B2 | 1/2012 | Zhou et al. |
| 8,147,448 B2 | 4/2012 | Sundar et al. |
| 8,149,131 B2 | 4/2012 | Blomquist |
| 8,152,486 B2 | 4/2012 | Fathallah et al. |
| 8,219,413 B2 | 7/2012 | Martinez et al. |
| 8,256,984 B2 | 9/2012 | Fathallah et al. |
| 8,258,973 B2 | 9/2012 | Newkirk |
| 8,286,977 B2 | 10/2012 | Butler et al. |
| 8,313,308 B2 | 11/2012 | Lawless et al. |
| 8,315,885 B2 | 11/2012 | Krogh et al. |
| 8,317,698 B2 | 11/2012 | Lowery |
| 8,380,536 B2 | 2/2013 | Howard et al. |
| 8,403,908 B2 | 3/2013 | Jacobson et al. |
| 8,417,311 B2 | 4/2013 | Rule |
| 8,449,500 B2 | 5/2013 | DelCastillo et al. |
| 8,449,524 B2 | 5/2013 | Braig et al. |
| 8,491,523 B2 | 7/2013 | Thor et al. |
| 8,518,021 B2 | 8/2013 | Stewart et al. |
| 8,523,797 B2 | 9/2013 | Lowery et al. |
| 8,523,813 B2 | 9/2013 | Grispo et al. |
| 8,581,454 B2 | 11/2013 | Corrington et al. |
| 8,591,491 B2 | 11/2013 | Moy et al. |
| 8,657,778 B2 | 2/2014 | Ziegler et al. |
| 8,666,769 B2 | 3/2014 | Butler et al. |
| 8,731,960 B2 | 5/2014 | Butler et al. |
| 8,768,719 B2 | 7/2014 | Wehba et al. |
| 8,777,590 B2 | 7/2014 | Moy et al. |
| 8,801,656 B2 | 8/2014 | Lowery et al. |
| 8,926,562 B2 | 1/2015 | Fathallah et al. |
| 9,072,831 B2 | 7/2015 | Kelly et al. |
| 9,174,145 B2 | 11/2015 | Weissenbach et al. |
| 9,468,713 B2 | 10/2016 | Hoenninger, III |
| 9,545,475 B2 | 1/2017 | Borges et al. |
| 9,799,274 B2 | 10/2017 | Alberti et al. |
| 9,849,233 B1 | 12/2017 | Edwards et al. |
| 10,034,975 B2 | 7/2018 | McLennan et al. |
| 10,039,878 B2 | 8/2018 | Gamelin |
| D830,546 S | 10/2018 | Lacy et al. |
| 10,143,795 B2 | 12/2018 | Chen |
| 10,260,161 B2 | 4/2019 | Rauenbusch et al. |
| 10,918,787 B2 | 2/2021 | Shubinsky et al. |
| 2001/0007932 A1 | 7/2001 | Kamen et al. |
| 2001/0009610 A1 | 7/2001 | Augustine et al. |
| 2001/0044602 A1 | 11/2001 | Angersbach et al. |
| 2002/0004015 A1 | 1/2002 | Carlisle et al. |
| 2002/0013551 A1 | 1/2002 | Zaitsu et al. |
| 2002/0096608 A1 | 7/2002 | Cedarberg |
| 2002/0099334 A1 | 7/2002 | Hanson et al. |
| 2002/0120229 A1 | 8/2002 | Miles et al. |
| 2002/0123741 A1 | 9/2002 | Rake et al. |
| 2003/0065537 A1 | 4/2003 | Evans |
| 2003/0127850 A1 | 7/2003 | Bischoff et al. |
| 2003/0138349 A1 | 7/2003 | Robinson et al. |
| 2003/0139701 A1 | 7/2003 | White et al. |
| 2003/0144574 A1 | 7/2003 | Heilman et al. |
| 2003/0175820 A1 | 9/2003 | Smith et al. |
| 2004/0025597 A1 | 2/2004 | Ericson |
| 2004/0074795 A1 | 4/2004 | Fischer |
| 2004/0082918 A1 | 4/2004 | Evans et al. |
| 2004/0176724 A1 | 9/2004 | Kamen et al. |
| 2004/0225409 A1 | 11/2004 | Duncan et al. |
| 2004/0232219 A1 | 11/2004 | Fowler |
| 2004/0249308 A1 | 12/2004 | Forssell |
| 2004/0251406 A1 | 12/2004 | Figueria |
| 2005/0006538 A1 | 1/2005 | Turi et al. |
| 2005/0055242 A1 | 3/2005 | Bello et al. |
| 2005/0059926 A1 | 3/2005 | Sage et al. |
| 2005/0074340 A1 | 4/2005 | Xu et al. |
| 2005/0095152 A1 | 5/2005 | Dale |
| 2005/0165384 A1 | 7/2005 | Gravesen et al. |
| 2005/0168941 A1 | 8/2005 | Sokol et al. |
| 2005/0171512 A1 | 8/2005 | Flaherty |
| 2005/0177110 A1 | 8/2005 | Azzolini |
| 2005/0209547 A1 | 9/2005 | Burbank et al. |
| 2005/0209563 A1 | 9/2005 | Hopping et al. |
| 2005/0260090 A1 | 11/2005 | Stark et al. |
| 2005/0268712 A1 | 12/2005 | Repko et al. |
| 2005/0274194 A1 | 12/2005 | Skinner et al. |
| 2006/0030821 A1 | 2/2006 | Lee et al. |
| 2006/0042633 A1 | 3/2006 | Bishop et al. |
| 2006/0070669 A1 | 4/2006 | Mabry et al. |
| 2006/0079831 A1 | 4/2006 | Gilbert |
| 2006/0136095 A1 | 6/2006 | Rob et al. |
| 2006/0142692 A1 | 6/2006 | Jacobson et al. |
| 2006/0173253 A1 | 8/2006 | Ganapathy et al. |
| 2006/0181695 A1 | 8/2006 | Sage, Jr. |
| 2006/0187069 A1 | 8/2006 | Duan |
| 2006/0189858 A1 | 8/2006 | Sterling et al. |
| 2006/0189925 A1 | 8/2006 | Gable et al. |
| 2006/0189926 A1 | 8/2006 | Hall et al. |
| 2006/0194325 A1 | 8/2006 | Gable et al. |
| 2006/0195045 A1 | 8/2006 | Gable et al. |
| 2006/0195058 A1 | 8/2006 | Gable et al. |
| 2006/0200070 A1 | 9/2006 | Callicoat et al. |
| 2006/0200071 A1 | 9/2006 | Sterling et al. |
| 2006/0200094 A1 | 9/2006 | Holz |
| 2006/0229531 A1 | 10/2006 | Goldberger et al. |
| 2006/0235348 A1 | 10/2006 | Callicoat et al. |
| 2006/0241550 A1 | 10/2006 | Kamen et al. |
| 2006/0260416 A1 | 11/2006 | Sage et al. |
| 2006/0266128 A1 | 11/2006 | Clark et al. |
| 2007/0038188 A1 | 2/2007 | Bialecki et al. |
| 2007/0060872 A1 | 3/2007 | Hall et al. |
| 2007/0112297 A1 | 5/2007 | Plahey et al. |
| 2007/0129618 A1 | 6/2007 | Goldberger et al. |
| 2007/0151366 A1 | 7/2007 | McDonald et al. |
| 2007/0179436 A1 | 8/2007 | Braig et al. |
| 2007/0225675 A1 | 9/2007 | Robinson et al. |
| 2007/0233003 A1* | 10/2007 | Radgowski ......... A61M 1/0058 604/151 |
| 2007/0239096 A1 | 10/2007 | Keenan et al. |
| 2007/0250339 A1 | 10/2007 | Mallett et al. |
| 2008/0039824 A1 | 2/2008 | Fathallah et al. |
| 2008/0051732 A1 | 2/2008 | Chen |
| 2008/0065420 A1 | 3/2008 | Tirinato et al. |
| 2008/0086042 A1 | 4/2008 | Brister et al. |
| 2008/0086044 A1 | 4/2008 | Brister et al. |
| 2008/0097288 A1 | 4/2008 | Levin et al. |
| 2008/0108942 A1 | 5/2008 | Brister et al. |
| 2008/0116157 A1 | 5/2008 | Fulbrook et al. |
| 2008/0145249 A1 | 6/2008 | Smisson |
| 2008/0208103 A1 | 8/2008 | Demers et al. |
| 2009/0004767 A1 | 1/2009 | Parks et al. |
| 2009/0018483 A1 | 1/2009 | Walker et al. |
| 2009/0046402 A1 | 2/2009 | Malkus et al. |
| 2009/0069743 A1 | 3/2009 | Krishnamoorthy et al. |
| 2009/0105646 A1 | 4/2009 | Hendrixson et al. |
| 2009/0143711 A1 | 6/2009 | Braig et al. |
| 2009/0240123 A1 | 9/2009 | Siebrecht et al. |
| 2010/0137778 A1 | 6/2010 | Kunjan et al. |
| 2010/0152681 A1 | 6/2010 | Mathias |
| 2010/0280486 A1 | 11/2010 | Khair et al. |
| 2011/0005606 A1 | 1/2011 | Bartels et al. |

(56) References Cited

U.S. PATENT DOCUMENTS

| | | |
|---|---|---|
| 2011/0015610 A1 | 1/2011 | Plahey et al. |
| 2011/0060199 A1 | 3/2011 | Robinson et al. |
| 2011/0060758 A1 | 3/2011 | Schlotterbeck et al. |
| 2011/0106462 A1 | 5/2011 | Kilburn et al. |
| 2011/0213395 A1 | 9/2011 | Corrington et al. |
| 2011/0264043 A1 | 10/2011 | Kotnick et al. |
| 2011/0264044 A1 | 10/2011 | Bartz et al. |
| 2011/0313318 A1 | 12/2011 | Rule et al. |
| 2011/0313358 A1 | 12/2011 | Hariharesan et al. |
| 2012/0035418 A1 | 2/2012 | Talbert et al. |
| 2012/0065482 A1 | 3/2012 | Robinson et al. |
| 2012/0078218 A1 | 3/2012 | Barnes |
| 2012/0130341 A1 | 5/2012 | Whitley |
| 2012/0145616 A1 | 6/2012 | Weissenbach et al. |
| 2012/0245554 A1 | 9/2012 | Kawamura |
| 2012/0271226 A1 | 10/2012 | Farrell et al. |
| 2013/0079710 A1 | 3/2013 | Krogh et al. |
| 2013/0165900 A1 | 6/2013 | Braig et al. |
| 2013/0177455 A1 | 7/2013 | Kamen et al. |
| 2013/0274669 A1 | 10/2013 | Stempfle et al. |
| 2013/0281965 A1 | 10/2013 | Kamen et al. |
| 2013/0297330 A1 | 11/2013 | Kamen et al. |
| 2015/0005935 A1 | 1/2015 | Bae et al. |
| 2015/0133861 A1 | 5/2015 | McLennan et al. |
| 2015/0167651 A1 | 6/2015 | Balteanu et al. |
| 2019/0059859 A1 | 2/2019 | Pinch |
| 2019/0060539 A1 | 2/2019 | Siess et al. |
| 2021/0202059 A1 | 7/2021 | Shubinsky et al. |

FOREIGN PATENT DOCUMENTS

| | | |
|---|---|---|
| DE | 37 42 268 | 6/1989 |
| EP | 0 197 705 | 10/1986 |
| EP | 0 306 130 | 3/1989 |
| EP | 0 396 003 | 11/1990 |
| EP | 0 423 978 | 4/1991 |
| EP | 0 429 866 | 6/1991 |
| EP | 0 447 985 | 9/1991 |
| EP | 0 450 736 | 10/1991 |
| EP | 0 483 794 | 5/1992 |
| EP | 0 510 881 | 10/1992 |
| EP | 0 569 030 | 11/1993 |
| EP | 0 477 551 | 1/1995 |
| EP | 0 481 656 | 8/1995 |
| EP | 0 697 898 | 2/1996 |
| EP | 0 839 062 | 5/1998 |
| EP | 0 891 784 | 1/1999 |
| EP | 0 960 627 | 12/1999 |
| EP | 1 177 802 | 2/2002 |
| EP | 2 742 961 | 6/2014 |
| JP | 01-265973 | 10/1989 |
| JP | 02-093917 | 7/1990 |
| JP | 09-327512 | 12/1997 |
| JP | 10-239193 | 9/1998 |
| JP | 2002-119587 | 4/2002 |
| JP | 3102285 | 3/2004 |
| JP | 2007-071695 | 3/2007 |
| JP | 2008-539964 | 11/2008 |
| JP | 4322661 | 6/2009 |
| JP | 2012-010718 | 1/2012 |
| JP | D1467576 | 4/2013 |
| JP | 2014-104011 | 6/2014 |
| TW | D192262 | 8/2018 |
| WO | WO 91/016087 | 10/1991 |
| WO | WO 92/017226 | 10/1992 |
| WO | WO 93/005829 | 4/1993 |
| WO | WO 93/012828 | 7/1993 |
| WO | WO 94/009847 | 5/1994 |
| WO | WO 95/024229 | 9/1995 |
| WO | WO 95/031233 | 11/1995 |
| WO | WO 96/035472 | 11/1996 |
| WO | WO 98/013080 | 4/1998 |
| WO | WO 99/010028 | 3/1999 |
| WO | WO 99/010830 | 3/1999 |
| WO | WO 00/057941 | 10/2000 |
| WO | WO 00/066203 | 11/2000 |
| WO | WO 01/039816 | 6/2001 |
| WO | WO 02/027276 | 4/2002 |
| WO | WO 02/036044 | 5/2002 |
| WO | WO 02/103209 | 6/2002 |
| WO | WO 02/087664 | 11/2002 |
| WO | WO 2004/069095 | 8/2004 |
| WO | WO 2004/070994 | 8/2004 |
| WO | WO 2005/000378 | 1/2005 |
| WO | WO 2005/082450 | 9/2005 |
| WO | WO 2005/118015 | 12/2005 |
| WO | WO 2007/008692 | 1/2007 |
| WO | WO 2007/124070 | 11/2007 |
| WO | WO 2008/144575 | 11/2008 |
| WO | WO 2009/021705 | 2/2009 |
| WO | WO 2009/039203 | 3/2009 |
| WO | WO 2009/039214 | 3/2009 |
| WO | WO 2010/048644 | 4/2010 |
| WO | WO 2011/159956 | 12/2011 |
| WO | WO 2014/131729 | 9/2014 |
| WO | WO 2017/144366 | 8/2017 |
| WO | WO 2020/214717 | 10/2020 |

OTHER PUBLICATIONS

"Differential Pressure Transmitter, Series PD-39 X", SensorsOne Ltd., Advertisement, Dec. 2005, pp. 2.

Galt et al., "Personal Digital Assistant-Based Drug Information Sources: Potential to Improve Medication Safety", Journal of Medical Library Association, Apr. 2005, vol. 93, No. 2, pp. 229-236.

Kutschka et al., "A New Minimized Perfusion Circuit Provides Highly Effective Ultrasound Controlled Deairing", Artificial Organs, 2007, vol. 31, No. 3, pp. 215-220.

Merry et al., "A New, Safety-Oriented, Integrated Drug Administration and Automated Anesthesia Record System", Anesthesia & Analgesia, Aug. 2001, vol. 93, No. 2 pp. 385-390.

Palanchon et al., "Acoustical Bubble Trapper Applied to Hemodialysis", Ultrasound in Medicine & Biology, Apr. 2008, vol. 34, No. 4, pp. 681-684.

Parlex, "Medical Device Product Examples", Johnson Medtech, Published at least as early as May 2008, pp. 2.

Stegmayr et al., "Development of Air Micro Bubbles in the Venous Outlet Line: An In Vitro Analysis of Various Air Traps Used for Hemodialysis", Artificial Organs, 2007, vol. 31, No. 6, pp. 483-488.

* cited by examiner

THERMAL MANAGEMENT SYSTEM AND METHOD FOR MEDICAL DEVICES

FIELD OF THE DISCLOSURE

The disclosure relates to a system and method for providing thermal management in medical devices.

BACKGROUND OF THE DISCLOSURE

Medical devices, such as infusion pumps, typically generate substantial heat. Certain medical electrical equipment standards, such as IEC 60601-1 $3^{rd}$ Edition, require the temperature of external surfaces of the medical device to not exceed specified limits to prevent discomfort to the user. For example, IEC 60601-1 $3^{rd}$ Edition requires the temperature of touchable molded plastic surfaces of the medical device to be 60 degrees Celsius or below under certain ambient and use conditions. Some conventional approaches to meeting this requirement are to place a fan within the housing, or to place air vents in one or more outer walls of the housing to dissipate the heat generated by the infusion pump circuitry. However, a fan requires additional power and air vents may allow fluid to enter the housing.

A safe, efficient, and low cost system and method of dissipating heat in a medical device is needed.

SUMMARY OF THE DISCLOSURE

In one embodiment of the disclosure, a medical device is disclosed. The medical device includes a housing, a power supply, a thermally conductive mounting clamp, a heat shield, and at least one fastener. The housing includes a handle. The power supply is disposed within the housing. The thermally conductive mounting clamp is attached to an outer surface of the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by the power supply is configured to dissipate from the power supply, through the heat shield, through the at least one fastener, and into the thermally conductive mounting clamp.

In another embodiment of the disclosure, an infusion device for mounting to a pole is disclosed. The infusion device includes a housing, a thermally conductive mounting clamp, an infusion pump, a power supply, a heat shield, and at least one fastener. The housing includes a handle. The thermally conductive mounting clamp is attached to an outer surface of the housing and is configured to attach to a pole. The infusion pump is disposed within the housing. The power supply is disposed within the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by the power supply is configured to dissipate from the power supply, through the heat shield, through the at least one fastener, and into the thermally conductive mounting clamp.

In still another embodiment of the disclosure, a method is disclosed of dissipating heat in a medical device. Heat is dissipated from a power supply within a housing, through a heat shield disposed within the housing adjacent to the power supply and against at least one interior surface of a handle of the housing, through at least one fastener passing through at least one opening in the housing and in thermally conductive contact with a thermally conductive mounting clamp, and into the thermally conductive mounting clamp.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Figure 1:
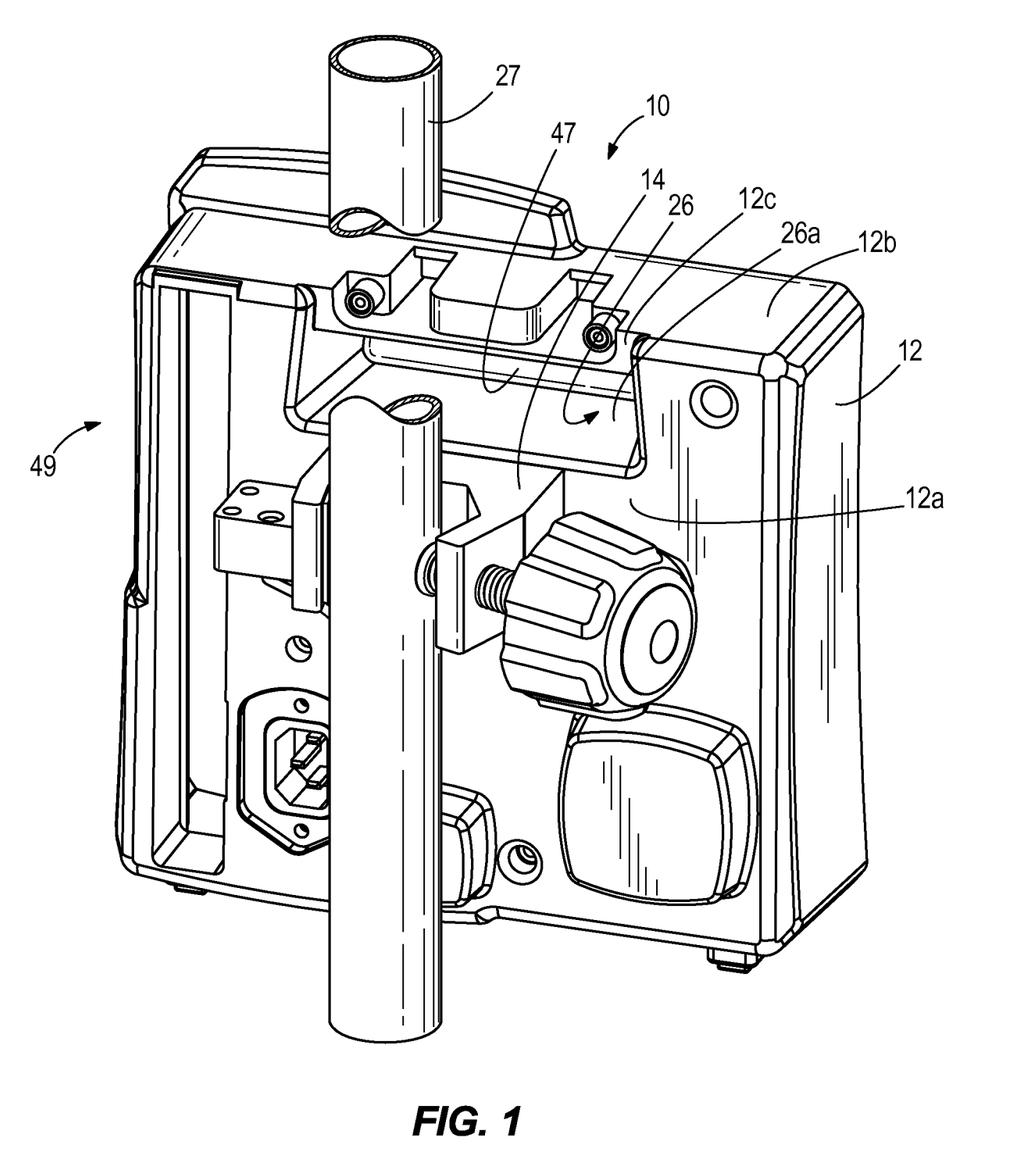
FIG. 1 illustrates a rear view of one embodiment of a medical device.
Figure 2:
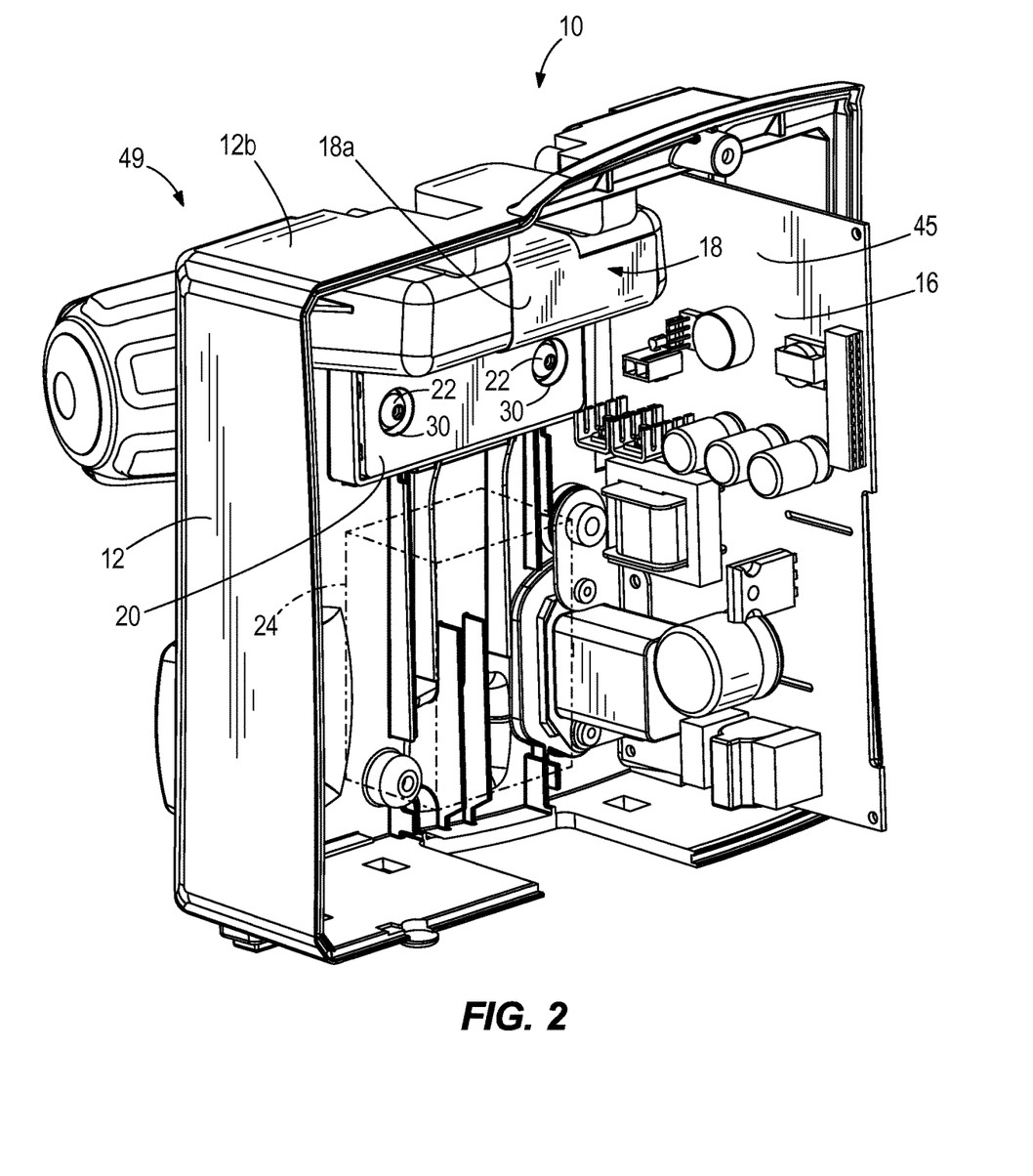
FIG. 2 illustrates a perspective cross-section view through the medical device of the embodiment of FIG. 1.
Figure 3:
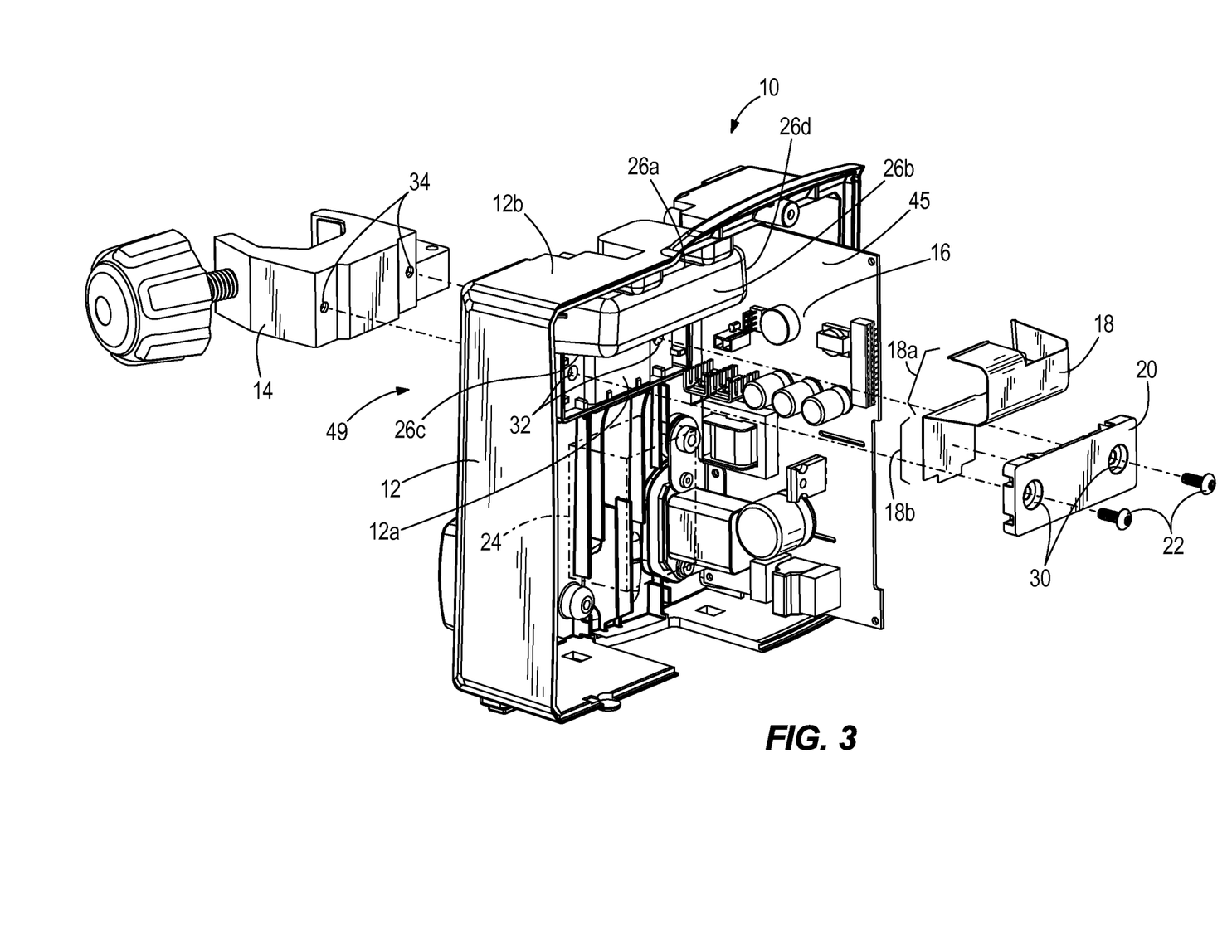
FIG. 3 illustrates a partially disassembled view of the perspective cross-section view of FIG. 2.

FIG. 1 illustrates a rear view of one embodiment of a medical device 10. FIG. 2 illustrates a perspective cross-section view through the medial device 10 of the embodiment of FIG. 1. FIG. 3 illustrates a partially disassembled view of the perspective cross-section view of FIG. 2. Collectively, as shown in FIGS. 1-3, the medical device 10 comprises a housing 12, a thermally conductive mounting clamp 14, a power supply 16, a heat shield 18, an electrically insulating thermally conductive bracket 20, fasteners 22, and infusion pump 24 supported by the housing 12. In other embodiments, the medical device 10 may comprise varying types of medical device unrelated to infusion pumps.

The housing 12 is made of Polycarbonate/Acrylonitrile Butadiene Styrene (PC/ABS). In other embodiments, the housing 12 may be made of varying materials. The housing 12 comprises a handle 26 external to the housing 12. The handle 26 may be gripped by a user to carry the medical device 10. In one embodiment the handle 26 is defined at least partially by a recess 26a formed in an outer surface 12a of the housing 12 adjacent to its top 12b. The recess 26a is elongated horizontally and is sized, shaped, and located to allow a typical user to insert one or more fingers into the recess 26a to move or lift the medical device 10. Since the recess 26a is adjacent to the top 12b of the housing 12, the user can also use their thumb on the top 12b of the housing 12 to improve their grip on the medical device 10. The thermally conductive mounting clamp 14 is attached to the outer surface 12a of the housing 12. The thermally conductive mounting clamp 14 allows the medical device 10 to be clamped to a structure 27 such as a pole. The thermally conductive mounting clamp 14 is made of aluminum. In other embodiments, the thermally conductive mounting clamp 14 may be made of other thermally conductive materials. The power supply 16 is disposed within the housing 12. The power supply 16 supplies power to the infusion pump 24.

The heat shield 18 is made of aluminum. The heat shield 18 is disposed within the housing 12 adjacent but apart from the power supply 16. A top portion 18*a* of the heat shield 18 comprises a curved, U-shape and is disposed against multiple interior surfaces 26*a*, 26*b*, 26*c*, and 26*d* of the handle 26. A bottom portion 18*b* of the heat shield 18 is straight. The bottom portion 18*b* of the heat shield 18 is disposed below the handle 26 sandwiched against and between an interior surface 12*a* of the housing 12 and the electrically insulating thermally conductive bracket 20. In other embodiments, the heat shield 18 may comprise varying shapes, may be made of varying thermally conductive materials, and may be disposed against any number and configuration of interior surfaces of the handle 26 or housing 12. The electrically insulating thermally conductive bracket 20 is made of a ceramic filled nylon. Preferably the thermally conductive bracket 20 comprises a plastic bracket material such as 299×131034 Nylon 6/6 supplied by RTP Company based out of Winona, Minn. In other embodiments, the electrically insulating thermally conductive bracket 20 may be made of varying electrically insulating but thermally conductive materials.

The fasteners 22 pass through openings 30 in the electrically insulating thermally conductive bracket 20, through openings 32 in the housing 12, into openings 34 in the thermally conductive mounting clamp 14 thereby securing the bottom portion 18*b* of the heat shield 18 between the electrically insulating thermally conductive bracket 20 and the interior surface 12*a* of the housing 12. In one embodiment at least the openings 34 in the thermally conductive mounting clamp 14 are threaded so as to matingly receive threaded fasteners 22. The fasteners 22 are in thermally conductive contact with the electrically insulating thermally conductive bracket 20 and with the mounting clamp 14. The fasteners 22 do not contact the heat shield 18. The fasteners 22 are made of steel. In other embodiments, the fasteners 22 may vary in number, may be made of varying thermally conductive materials, and may vary in configuration. Heat generated by the power supply 16 is configured to dissipate from the power supply 16 to the heat shield 18 through at least one of convection or radiation, and from the heat shield 18, through the electrically insulating thermally conductive bracket 20, through the fasteners 22, and into the thermally conductive mounting clamp 14 through conduction. In such manner, heat from the power supply 16 is dissipated using the configuration of the medical device 10 in order to cool the handle 26 to meet temperature requirements for the handle 26 of the housing 12 without requiring vents or a fan within the housing 12.

Figure 4A:
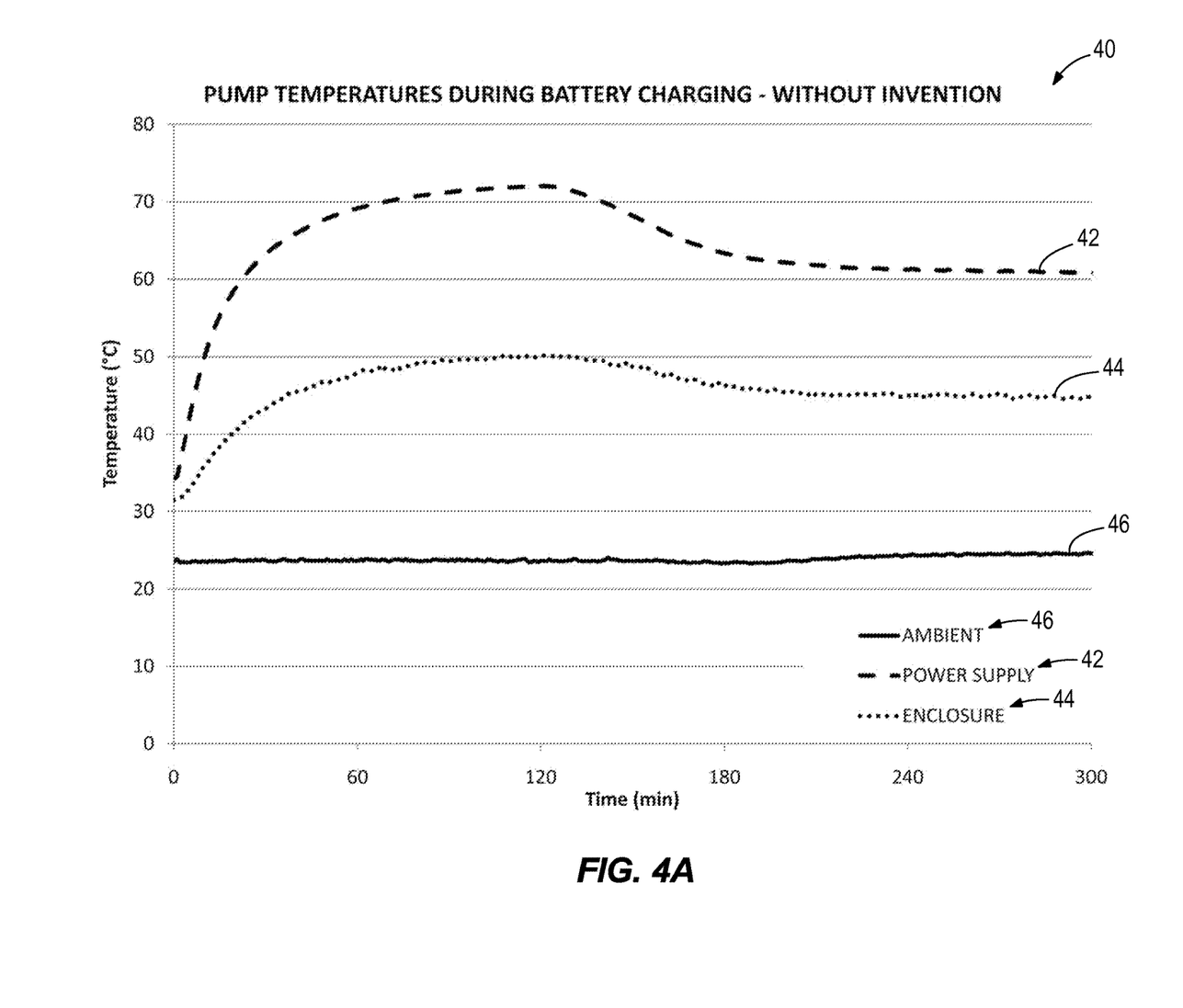
FIG. 4A illustrates a temperature versus time graph plotting temperature versus time curves which were obtained for a medical device identical to the medical device of FIGS. 1-3 but lacking the heat shield and the thermally conductive bracket of the disclosure.

FIG. 4A illustrates a temperature versus time graph 40 plotting temperature versus time curves 42, 44, and 46 which were obtained for a medical device identical to the medical device 10 of FIGS. 1-3 but lacking the heat shield 18 and the thermally conductive bracket 20 of the disclosure. Time is plotted on the X-axis in minutes and temperature is plotted on the Y-axis in degrees Celsius. Curve 42 represents the temperature versus time which was obtained, for the medical device identical to the medical device 10 of FIGS. 1-3 but lacking the heat shield 18 and the thermally conductive bracket 20 of the disclosure, at location 45 on the power supply 16 as shown in FIGS. 2 and 3 (although location 45 is shown on medical device 10 of the disclosure having the heat shield 18 and the thermally conductive bracket 20, the location tested in creating curve 42 for the medical device lacking the heat shield and the thermally conductive bracket is identical to location 45). Curve 44 represents the temperature versus time which was obtained, for the medical device identical to the medical device 10 of FIGS. 1-3 but lacking the heat shield 18 and the thermally conductive bracket 20 of the disclosure, at location 47 on the outer surface 12*a* of the housing 12 as shown in FIG. 1, and more specifically was obtained on a rear vertical exterior surface 12*c* of the recess 26*a* that defines the handle 26 (although location 47 is shown on medical device 10 of the disclosure having the heat shield 18 and the thermally conductive bracket 20, the location tested in creating curve 44 for the medical device lacking the heat shield and the thermally conductive bracket is identical to location 47). Curve 46 represents the temperature versus time which was obtained, for the medical device identical to the medical device 10 of FIGS. 1-3 but lacking the heat shield 18 and the thermally conductive bracket 20 of the disclosure, at location 49 which is the ambient temperature in the laboratory where the medical device 10 was tested as shown in FIGS. 1, 2, and 3 (although location 49 is shown on medical device 10 of the disclosure having the heat shield 18 and the thermally conductive bracket 20, the location tested in creating curve 46 for the medical device lacking the heat shield and the thermally conductive bracket is identical to location 49).

Figure 4B:
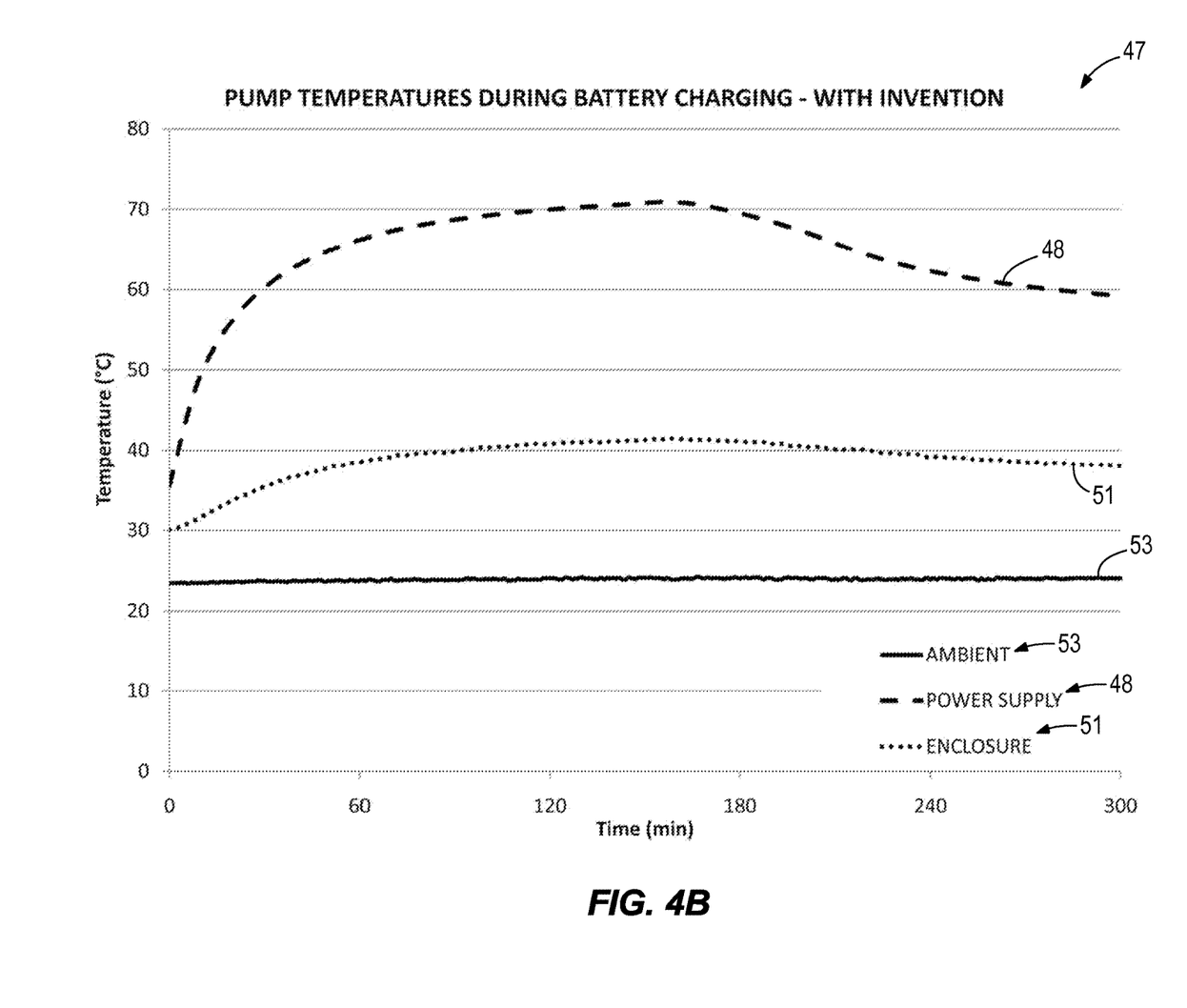
FIG. 4B illustrates a temperature versus time graph plotting temperature versus time curves which were obtained for the medical device of FIGS. 1-3 having the heat shield and the thermally conductive bracket of the disclosure.

FIG. 4B illustrates a temperature versus time graph 47 plotting temperature versus time curves 48, 51, and 53 which were obtained for the medical device 10 of FIGS. 1-3 having the heat shield 18 and the thermally conductive bracket 20 of the disclosure. Time is plotted on the X-axis in minutes and temperature is plotted on the Y-axis in degrees Celsius. Curve 48 represents the temperature versus time which was obtained, for the medical device 10 of FIGS. 1-3 having the heat shield 18 and the thermally conductive bracket 20 of the disclosure, at location 45 on the power supply 16 as shown in FIGS. 2 and 3. Curve 51 represents the temperature versus time which was obtained, for the medical device 10 of FIGS. 1-3 having the heat shield 18 and the thermally conductive bracket 20 of the disclosure, at location 47 on the outer surface 12*a* of the housing 12 as shown in FIG. 1, and more specifically obtained on a rear vertical exterior surface 12*c* of the recess 26*a* that defines the handle 26. A comparison of curve 44 of FIG. 4A to curve 51 of FIG. 4B demonstrates that the heat shield 18 and the thermally conductive bracket 20 of the medical device 10 of FIGS. 1-3 helped reduce the temperature obtained at location 47 on the outer surface 12*a* of the housing 12, and more specifically obtained on the rear vertical exterior surface 12*c* of the recess 26*a* that defines the handle 26 as shown in FIG. 1, to a level that meets the requirements of the IEC 60601-1 $3^{rd}$ Edition standard which requires the temperature of external surfaces of the housing 12 of the medical device 10 to be 60 degrees Celsius or below under certain ambient conditions. Curve 53 represents the temperature versus time which was obtained, for the medical device 10 of FIGS. 1-3 having the heat shield 18 and the thermally conductive bracket 20 of the disclosure, at location 49 which is the ambient temperature in the laboratory where the medical device 10 was tested as shown in FIGS. 1, 2, and 3.

Thus, it can be seen and appreciated by one of ordinary skill in the art that temperature versus time testing of an embodiment of a medical device lacking components of the present disclosure resulted in a temperature versus time curve at location 47 on the outer surface 12a of the housing 12 in or near the handle 26 which came close to not meeting the requirements of the IEC 60601-1 $3^{rd}$ Edition standard in an environment with an ambient temperature of approximately 25 degrees Celsius. One skilled in the art will appreciate that if the environment has an ambient temperature of 40 degrees Celsius and the medical device lacks the components of the present disclosure, the surface temperature may exceed the standard. Based on this testing, it is apparent that the use of the heat shield 18 and the thermally conductive bracket 20 allows the medical device 10 of FIGS. 1-3 to reduce its temperature to easily meet the IEC 60601-1 $3^{rd}$ Edition standard without the use of vents or a fan to lower the temperature. This reduces the power required by the medical device 10 along with reducing the likelihood that undesired fluid will enter the housing 12 of the medical device 10.

Figure 5:
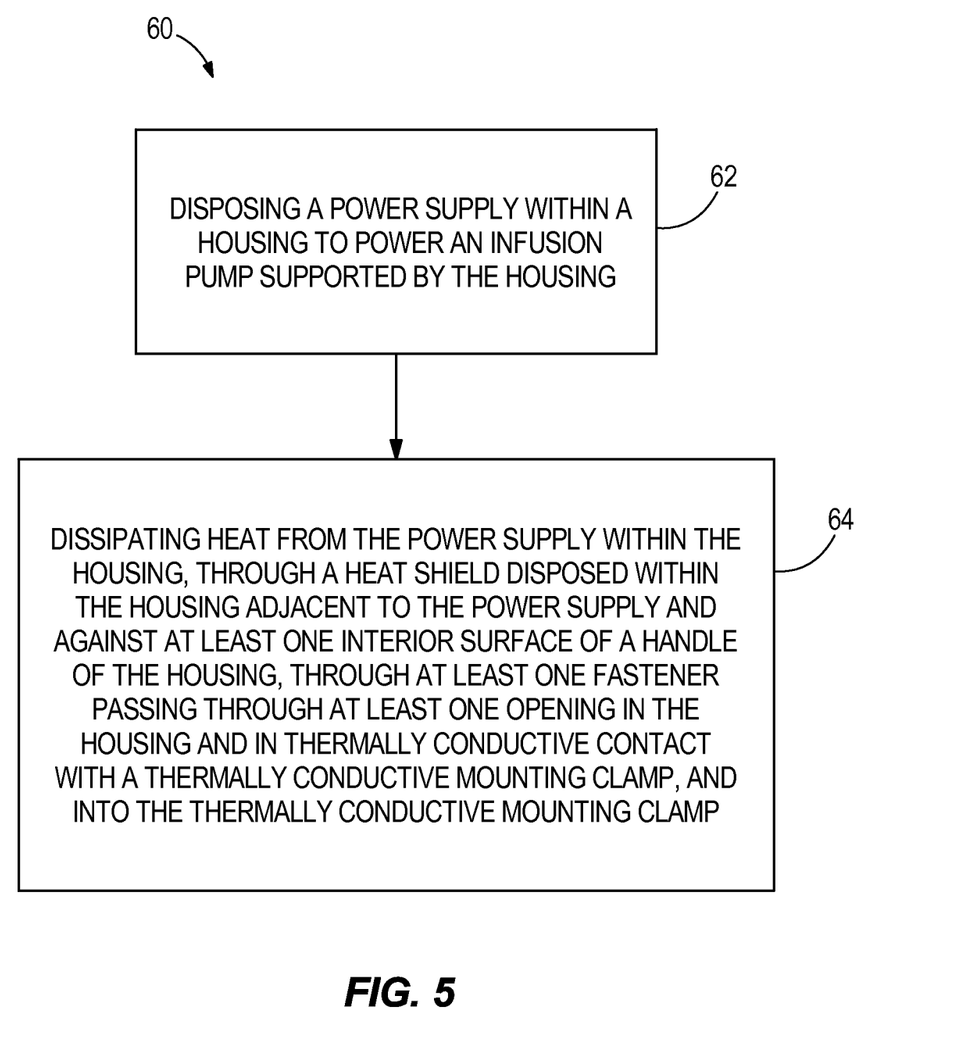
FIG. 5 illustrates a flowchart showing one embodiment of a method of dissipating heat in a medical device.

FIG. 5 illustrates a flowchart showing one embodiment of a method 60 of dissipating heat in a medical device. The method 60 may utilize any of the embodiments of the medical device disclosed herein. In step 62, a power supply disposed within a housing may power an infusion pump supported by the housing. In step 64, heat is dissipated from the power supply within the housing, through a heat shield disposed within the housing adjacent to the power supply and against at least one interior surface of a handle of the housing, through at least one fastener passing through at least one opening in the housing and in thermally conductive contact with a thermally conductive mounting clamp, and into the thermally conductive mounting clamp.

In one embodiment, step 64 may comprise the heat generated by the power supply being dissipated from the power supply to the heat shield through at least one of convection or radiation, and from the heat shield, through an electrically insulating thermally conductive bracket disposed against the heat shield within the housing, through the at least one fastener, and into the thermally conductive mounting clamp through conduction. The heat shield may be curved, may comprise a U-shape, and may be disposed against multiple interior surfaces of the handle of the housing. In other embodiments, the configuration, shape, materials, and number of components of the medical device may vary. In still other embodiments, any of the steps of the method 60 may be altered in substance or in order, may not be followed, or one or more additional steps may be added.

One or more embodiments of the disclosure may reduce one or more issues of one or more of the existing medical devices by dissipating heat generated by the medical device without requiring a fan or vents within the housing of the medical device. This may reduce the power required by the medical device along with reducing the likelihood that undesired fluid will enter the housing of the medical device.

It should be understood, of course, that the foregoing relates to exemplary embodiments of the disclosure and that modifications may be made without departing from the scope of the disclosure as set forth in the following claims.

We claim:

1. A medical device comprising:
a housing comprising a handle;
a power supply disposed within the housing, the power supply adjacent to a heat shield, the heat shield disposed within the housing;
a fastener passing through an opening in the housing, the fastener in thermally conductive contact with a thermally conductive mounting clamp, wherein heat generated by the power supply dissipates from the power supply into the heat shield and into the handle, the heat shield conducts heat away from the handle and from the power supply into the fastener, the heat passing from the fastener into the thermally conductive mounting clamp.

2. The medical device of claim 1, further comprising an infusion pump supported by the housing.

3. The medical device of claim 1, wherein the thermally conductive mounting clamp comprises aluminum.

4. The medical device of claim 1, wherein the heat shield is disposed apart from the power supply within the housing, and the heat generated by the power supply is configured to dissipate from the power supply to the heat shield through convection or radiation and from the heat shield, through the fastener, and into the thermally conductive mounting clamp through conduction.

5. The medical device of claim 1 wherein the heat shield comprises aluminum.

6. The medical device of claim 1 wherein the heat shield comprises a curved U-shape.

7. The medical device of claim 1 wherein the heat shield is positioned against multiple interior surfaces of the handle.

8. The medical device of claim 1 further comprising an electrically insulating, thermally conductive bracket disposed against the heat shield within the housing, wherein heat generated by the power supply is configured to dissipate from the power supply, through the heat shield, through the electrically insulating, thermally conductive bracket, through the fastener, and into the thermally conductive mounting clamp.

9. The medical device of claim 8, wherein the thermally conductive bracket comprises a ceramic filled nylon.

10. The medical device of claim 1, wherein the thermally conductive mounting clamp comprises a hole, the hole configured to matingly receive the fastener.

11. The medical device of claim 10, wherein the hole is threaded.

12. The medical device of claim 1, wherein the housing does not enclose a fan.

13. The medical device of claim 12, wherein the housing does not comprise a heat vent.

14. A method of dissipating heat in a medical device, comprising:
dissipating heat from a power supply within a housing into a heat shield adjacent a handle, the heat passing from the heat shield through an electrically insulating, thermally conductive bracket disposed against the heat shield into a fastener, the fastener passing through an opening in the housing and in thermally conductive contact with a thermally conductive mounting clamp, the heat passing from the fastener into the thermally conductive mounting clamp.

15. The method of claim 14, further comprising the power supply powering an infusion pump supported by the housing.

16. The method of claim 14, further comprising the heat generated by the power supply dissipating from the power supply to the heat shield through at least one of convection or radiation and from the heat shield, through the fastener, and into the thermally conductive mounting clamp through conduction.

17. The method of claim 14, wherein the heat shield is disposed against multiple interior surfaces of the handle.

18. The method of claim 14, wherein the heat shield comprises a curved, U-shape.

* * * * *